United States Patent
Ito et al.

(10) Patent No.: US 8,529,439 B2
(45) Date of Patent: Sep. 10, 2013

(54) ENDOSCOPIC SYSTEM

(75) Inventors: Yoshiaki Ito, Fuchu (JP); Manabu Miyamoto, Musashino (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 1232 days.

(21) Appl. No.: 12/367,703

(22) Filed: Feb. 9, 2009

(65) Prior Publication Data

US 2009/0259100 A1    Oct. 15, 2009

Related U.S. Application Data

(60) Provisional application No. 61/046,537, filed on Apr. 21, 2008.

(30) Foreign Application Priority Data

Apr. 11, 2008    (JP) ................. 2008-103766

(51) Int. Cl.
*A61B 1/00* (2006.01)
*A61B 1/04* (2006.01)
*A61B 1/06* (2006.01)
*A61B 1/12* (2006.01)

(52) U.S. Cl.
USPC ............ 600/156; 600/112; 600/132; 600/172

(58) Field of Classification Search
USPC ................. 600/121–125, 131, 132, 156, 172, 600/175, 112–114, 130
See application file for complete search history.

(56) References Cited

U.S. PATENT DOCUMENTS

| 4,853,773 A | 8/1989 | Hibino et al. |
| 4,860,094 A * | 8/1989 | Hibino et al. ............ 600/109 |

(Continued)

FOREIGN PATENT DOCUMENTS

| EP | 1 623 664 A1 | 2/2006 |
| JP | 57-20247 A | 2/1982 |

(Continued)

OTHER PUBLICATIONS

Japanese Office Action dated Aug. 21, 2012 (and English translation thereof) in counterpart Japanese Application No. 2008-103766.

(Continued)

*Primary Examiner* — Katherine Dowe
*Assistant Examiner* — Aaron B Fairchild
(74) *Attorney, Agent, or Firm* — Holtz, Holtz, Goodman & Chick, PC

(57) ABSTRACT

An endoscopic system is composed by connecting an endoscope and peripheral equipment. The endoscope has an endoscope main body, and an imaging unit, which is slender imaging optics. The endoscope is constructed so that the endoscope main body and imaging unit are freely connectable and separable. The endoscope main body has an insertion part which is inserted into an abdominal cavity, a branch member, which is a middle end of the endoscope main body, and provided in a proximal end portion of the insertion part, a first extension part provided in the proximal end portion of the branch member, a main body operation unit provided in a proximal end portion of the first extension part, a universal cord, and a connection unit, which is provided in a proximal end portion of the universal cord, and is connected to the peripheral equipment.

12 Claims, 15 Drawing Sheets

(56) References Cited

U.S. PATENT DOCUMENTS

| | | | |
|---|---|---|---|
| 5,178,130 A * | 1/1993 | Kaiya | 600/109 |
| 5,489,256 A | 2/1996 | Adair | |
| 5,630,782 A | 5/1997 | Adair | |
| 6,095,970 A * | 8/2000 | Hidaka et al. | 600/110 |
| 2006/0052663 A1 | 3/2006 | Koitabashi | |
| 2006/0116550 A1 * | 6/2006 | Noguchi et al. | 600/132 |

FOREIGN PATENT DOCUMENTS

| | | |
|---|---|---|
| JP | 64-24215 A | 1/1989 |
| JP | 64-68711 A | 3/1989 |
| JP | 3-4830 A | 1/1991 |
| JP | 3-289769 A | 12/1991 |
| JP | 4-39854 B2 | 6/1992 |
| JP | 6-30891 A | 2/1994 |
| JP | 6-296589 A | 10/1994 |
| JP | 9-70383 A | 3/1997 |
| JP | 2683386 B2 | 11/1997 |
| JP | 10-258022 A | 9/1998 |
| JP | 2000-14628 A | 1/2000 |
| JP | 2000-121961 A | 4/2000 |
| JP | 2001-390 A | 1/2001 |
| JP | 2004-141666 A | 5/2004 |
| JP | 2004-337311 A | 12/2004 |
| JP | 2007-236812 A | 9/2007 |

OTHER PUBLICATIONS

Extended European Search Report dated Jul. 31, 2009 (4 pages), issued in counterpart European Application Serial No. 09152380.3.

* cited by examiner

ENDOSCOPIC SYSTEM

CROSS-REFERENCE TO RELATED APPLICATIONS

This application claims the benefit of U.S. Provisional. Application No. 61/046,537, filed Apr. 21, 2008.

This application is based upon and claims the benefit of priority from prior Japanese Patent Application No. 2008-103766, filed Apr. 11, 2008, the entire contents of which are incorporated herein by reference.

BACKGROUND OF THE INVENTION

1. Field of the Invention The present invention relates to an endoscopic system having an endoscope provided with separable imaging optics.

2. Description of the Related Art

Generally, when a used medical device such as an endoscope is reused, diseases infected by using the medical device must be prevented. Therefore, in a hospital and other medical institution, a used medical device is cleaned and disinfected. An insertion part of an endoscope has a treatment device insertion channel. Therefore, certain time is needed to clean and disinfect an endoscope.

An endoscope disclosed in Jpn. Pat. Appln. KOKAI Publication No. 2007-236812 can be used for endoscopy continuously and repeatedly without cleaning and disinfections after every time of use.

An endoscope disclosed in Jpn. Pat. Appln. KOKAI Publication No. 2004-141666 can reduce dimensions and weight of an operation unit, provide excellent operability, and reduce an operator's fatigue. In the endoscope disclosed in the patent application No. 2004-141666, a branch unit is provided at a near end of an insertion part. One end of the branch unit is connected to an operation unit through a flexible cord. The other end of the branch unit is connected to a connection unit through a universal cord. The connection unit is connected to peripheral equipment. A solid imaging element, which is a part of an imaging unit, is inserted into the insertion part and universal cord. The solid imaging element is inserted into the universal cord through the insertion part, and is connected to the peripheral equipment through the connection unit.

BRIEF SUMMARY OF THE INVENTION

The present invention provides an endoscopic system, in which an endoscope is easily connected to peripheral equipment, and an imaging unit is separable from an endoscope.

According to an aspect of the invention, there is provided an endoscopic system comprising an endoscope main body in which an air-feed piping, a liquid-feed piping and a suction piping are inserted; an imaging unit which is connectable to or separable from the endoscope main body; a branch member which is provided in the endoscope main body, and has an opening for freely inserting or removing the imaging unit into/from the endoscope main body, when the imaging unit is connected to or separated from the endoscope main body; peripheral equipment which has a light source for generating illumination light for photographic shooting, and a display unit for displaying an image captured by the imaging unit; a piping connector which is provided in the endoscope main body through a universal cord, connects the imaging unit, has a peripheral equipment side connector to connect the peripheral equipment, and connects the air-feed piping, liquid-feed piping and suction piping inserted into the universal cord, to the peripheral equipment, by connecting the peripheral equipment through the peripheral equipment side connector; a universal cord connector which is provided on the piping connector side of the universal cord, and is connected to the piping connector; a separate imaging connector which is provided on the piping connector side of the imaging unit, and connects the piping connector; and a wiring connector which is branched from the piping connector, and connects electrical wiring in the imaging unit and electrical wiring in the endoscope main body, to the peripheral equipment.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of the invention will be explained in detail with reference to the accompanying drawings.

A first embodiment will be explained by referring to FIGS. 1 to 7 and FIGS. 8A to 8E.

Figure 1:
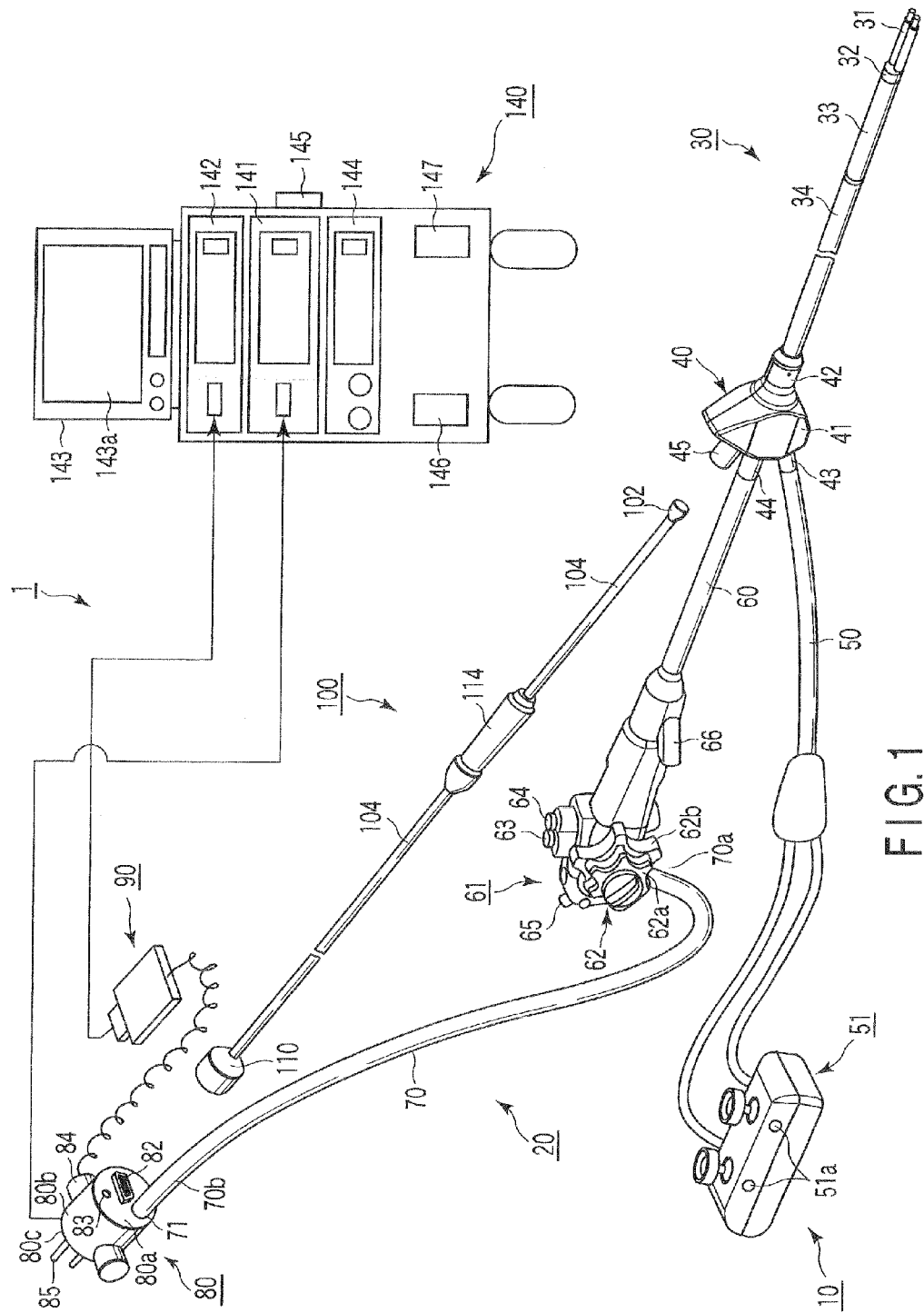
FIG. 1 is a diagram showing a configuration of an endoscopic system according to a first embodiment of the invention.

As shown in FIG. 1, an endoscopic system 1 is composed by connecting an endoscope 10 and peripheral equipment 140.

As shown in FIG. 1, the endoscope 10 has an endoscope main body 20, and an imaging unit 100, which is slender imaging optics. In the endoscope 10, the endoscope main body 20 and imaging unit 100 are freely connectable and separable. Specifically, the imaging unit 100 can freely be inserted or removed from the endoscope main body 20.

The endoscope main body 20 has an insertion part 30 to be inserted into an abdominal cavity; a branch member 40 which is a middle end of the endoscope main body 20, and provided in a proximal end portion of the insertion part 30; first extension part 60 and second extension part 50 provided in a proximal end portion of the branch member 40; a distal end operation unit 51 provided in a proximal end portion of the second extension part 50; a main body operation unit 61 provided in a proximal end portion of the first extension part 60; a universal cord 70 extended from the main body operation unit 61; a connection unit 80 which is provided in a proximal end portion of the universal cord 70, and is used to connect a light source unit 141, an image display unit 143 and a control unit 144 of peripheral equipment 140; and an imaging connector 90 which connects the connection unit 80 and an image-processing unit 142 in the peripheral equipment 140.

A distal end (an imaging module 102) of the imaging unit 100 is inserted into the insertion part 30 through the branch member 40, and is arranged on the distal end side of the insertion part 30. A proximal end (a separate imaging connector 110) of the imaging unit 100 is removably connected to the connection unit 80.

First, the insertion part 30 will be explained.

The insertion part 30 has two distal end bending parts 31, for example, arranged on the most distal end side of the insertion part 30, a distal end portion 32 arranged at the proximal ends of the distal end bending parts 31, a main body bending part 33 connected to the proximal end of the distal end portion 32, and a flexible tube part (a connecting tube part) 34, which is arranged on the most proximal end side of the insertion part 30, and is connected to the proximal end of the main body bending part 33.

Figure 8A:
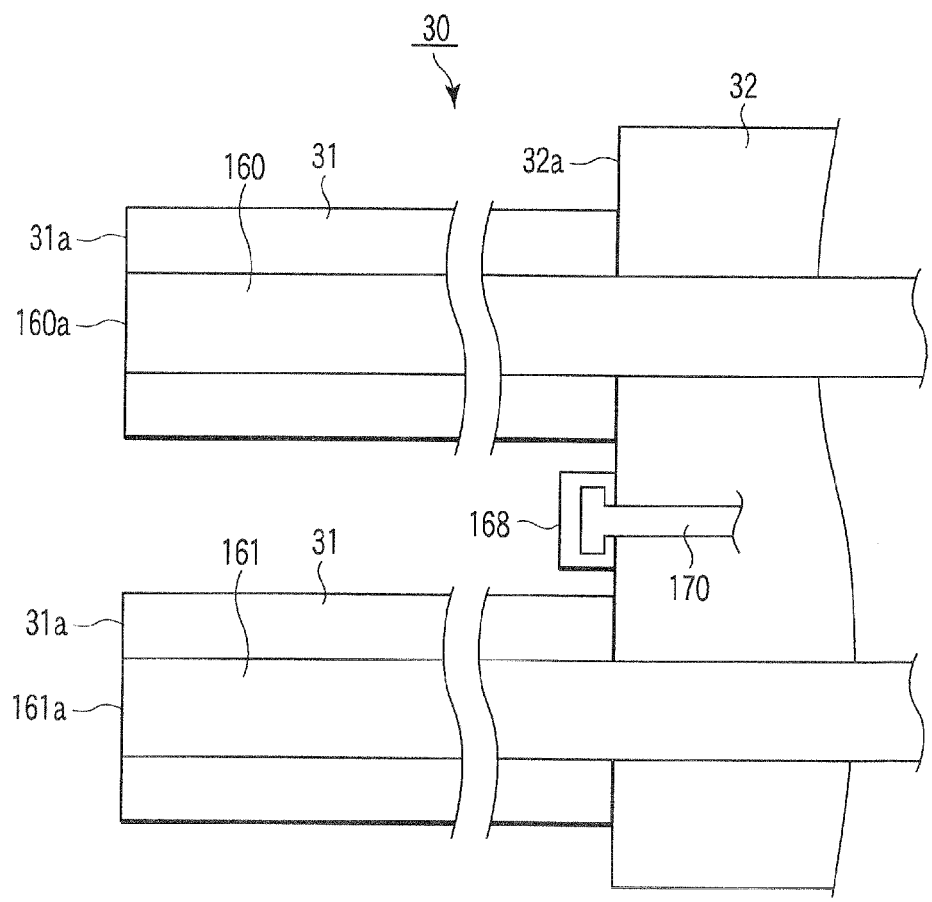
FIG. 8A is a schematic diagram showing an internal structure of a distal end bending part.
Figure 8B:
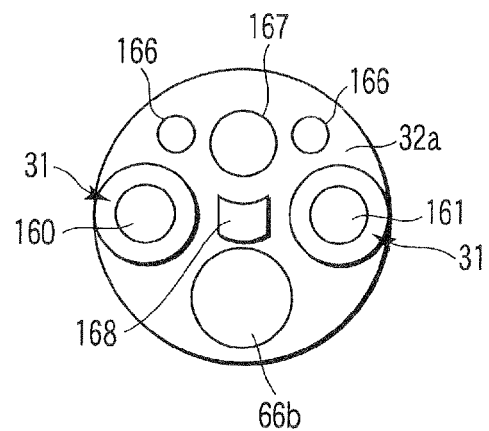
FIG. 8B is a schematic front view of a main body bending part.

The distal end bending part 31 is operated by the distal end operation unit 51, bendable at least in one direction, and has a bending mechanism for bending. The distal end bending part 31 is arranged as a pair on a distal end face 32a of the distal end portion 32, as shown in FIGS. 8A and 8B. The distal end face 31a of the distal end bending part 31 has exit ports 160a and 161a of channel tubes 160 and 161 to be described later, as shown in FIG. 8A. A not-shown distal end treatment device is projected from the exit ports 160a and 161a (explained later in detail).

The main body bending part 33 is bent in four up/down/left/right directions by the main body operation unit 61. Specifically, a not-shown operation wire is pulled and driven by rotating a left/right bending operation knob 62a and an up/down operation knob 62b, as described later. Thereby, the main body bending part 33 is remotely bent from a normal linear state (a not-bent state) extending at a bending angle of 0°, to a bent state in which it is bent in an up/down/left/right direction at a desired bending angle. The main unit being part 33 is preferably bent in only two directions.

A not-shown operation wire is extended from the main body operation unit 61 to the main body bending part 33 through the first extension part 60 and branch member 40. The operation wire is guided to the main body bending part 33 by a not-shown wire guide member, such as a coil, provided in the flexible tube part 34, for example. The operation wire is protected from other internal tubes (tubular members) by the wire guide member.

The flexible tube part 34 has a flex, a mesh-like braid provided outside the flex for covering the flex, and an outer sheath covering the braid.

The flex is made of a spirally formed thin belt-like stainless steel plate, for example, and is shaped substantially tubular. The flex is a thin-walled metallic spiral tube, for example.

The braid is made of woven bundles of stainless steel wires, and is shaped substantially tubular. The braid is a mesh-like tube, for example.

The outer sheath is made of flexible resin material such as rubber, and is shaped substantially tubular for covering the outside of the braid.

The flexible tube part 34 is connected to the branch member 40 at the proximal end.

Next, the branch member 40 will be explained.

Figure 2:
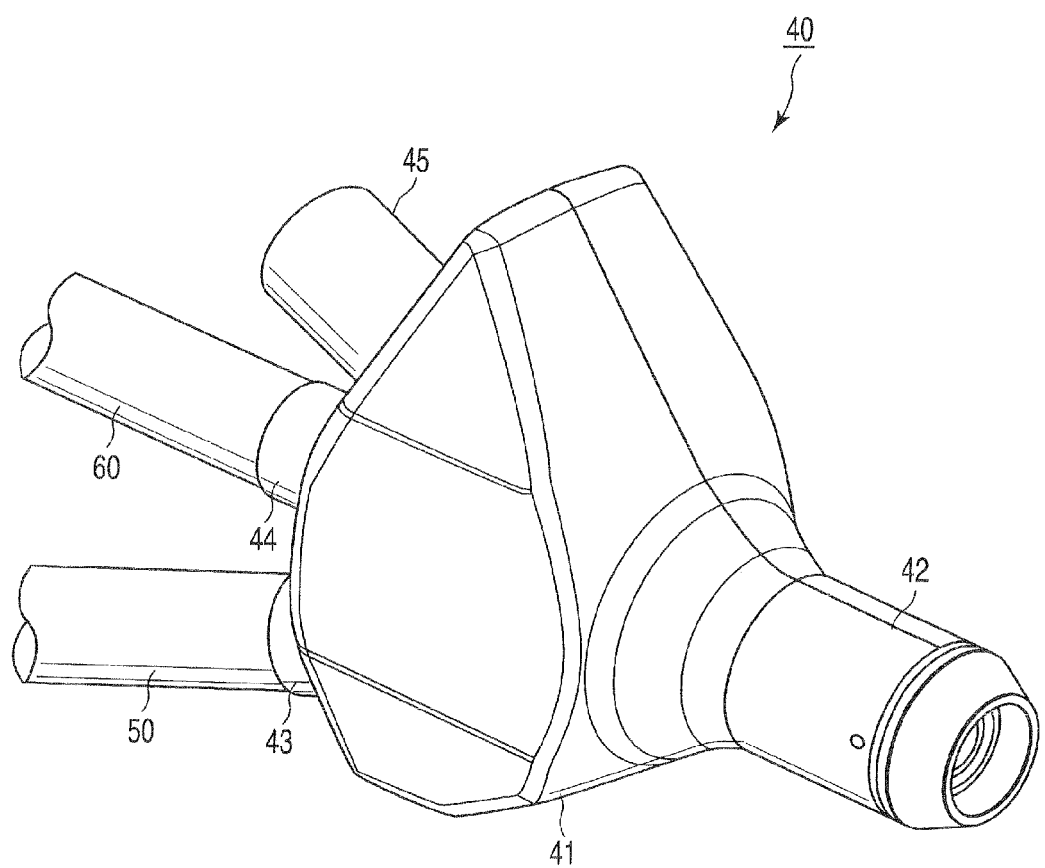
FIG. 2 is a perspective view of a branch member.

As shown in FIGS. 1 and 2, the branch member 40 has a branch main body 41, a flexible tube side opening 42 for connection of the flexible tube part 34, a second opening 43 for connection of the second extension part 50, a first opening 44 for connection of the first extension part 60, and a third opening 45 for removable connection of the imaging unit 100, as an inlet to insert the imaging unit 100 into the insertion part 30. The first, second and third openings 44, 43 and 45 are arranged in the branch main body 41, and are connected to the flexible tube side opening 42.

A proximal end of the flexible tube part 34 is inserted into the flexible tube side opening 42. A distal end of the second extension part 50 is inserted into the second opening 43. A distal end of the first extension part 60 is inserted into the first opening 44. The third opening 45 is used for inserting or removing the imaging unit 100 into/from the endoscope main body 20 (the insertion part 30), when the imaging unit 100 is connected to or separated from the endoscope main body 20.

As described above, the imaging unit 100 is removably connected to the endoscope main body 20 through the branch member 40, for convenience of cleaning. Namely, the imaging unit 100 is separable from the endoscope main body 20. Therefore, in this embodiment, the imaging unit 100 can be cleaned and disinfected more easily than the case in which the imaging unit 100 is incorporated in the endoscope 10 (not shown).

Next, the second extension part 50 and distal end operation unit 51 will be explained.

The second extension part 50 is extended from the branch member 40 in the flexible state. A proximal end of the second extension part 50 is branched into two parts, each of which is connected to the distal end operation unit 51. The channel tubes 160 and 161 are inserted into the second extension part 50.

The distal end operation unit 51 pulls a not-shown operation wire connected to the distal end bending part 31, thereby operating the distal end bending part 31. The distal end operation unit 51 has two channel openings 51a for inserting a not-shown distal end treatment device. A distal end treatment device is inserted into the channel openings 51a, and projected from the exit ports 160a and 161a through the channel tubes 160 and 161 inserted in the second extension part 50 and insertion part 30.

Next, the first extension part 60 and main body operation unit 61 will be explained.

The first extension part 60 is extended from the branch member 40 in the flexible state, and connected to the main body operation unit 61. A channel tube 66a is inserted into the first extension part 60.

The main body operation unit 61 is provided with a bending part operation knob 62 for bending the main body bending part 33.

The bending part operation knob 62 is provided with a left/right bending operation knob 62 for bending the main body bending part 33 to the right and left, and an up/down bending operation knob 62b for bending the main body bending part 33 up and down. The left/right bending operation knob 62a is connected to a not-shown left/right bending operation mechanism, which is driven by the left and right bending operation. The up/down bending operation knob 62b is connected to a not-shown up/down bending operation mechanism, which is driven by the up/down bending operation knob 62b. The up/down bending operation mechanism and left/right bending operation mechanism are provided in the main body operation unit 61, and is connected to a proximal end of a not-shown operation wire. A distal end of the operation wire is connected to the main body bending part 33. When the bending operation knob 62 is operated, the operation wire is pulled through the bending operation mechanism, and the main body bending part 33 is bent. The main body operation unit 61 bends the main body bending part 33 in this manner.

The main body operation unit 61 is also provided with a suction button 63, an air/water-feed button 64, buttons for photographic shooting 65, and a main body treatment device insertion part 66. The man body treatment device insertion part 66 is located at a position deviated from the axial direction of the first extension part 60.

The first extension part 60 and main body operation unit 61 are aligned with the center axis of the insertion part 30, by the branch member 40. When treatment is made, the proximal end portion of the insertion part 30 or first extension part 60 may be rotated about the axis. At this time, the first extension part 60 and main body operation unit 61 can transfer the rotational forces of the proximal end portion of the insertion part 30 and first extension part 60, to the distal end portion 32 of the insertion part 30, easier than the case in which the first extension part 60 and main body operation unit 61 are not aligned with the center axis of the insertion part 30. Namely, as the first extension part 60 and main body operation unit 61 are aligned with the center axis of the insertion part 30 by the branch member 40, operability of the endoscope 10 in making treatment can be kept high.

Next, the universal cord 70 will be explained.

Figure 3:
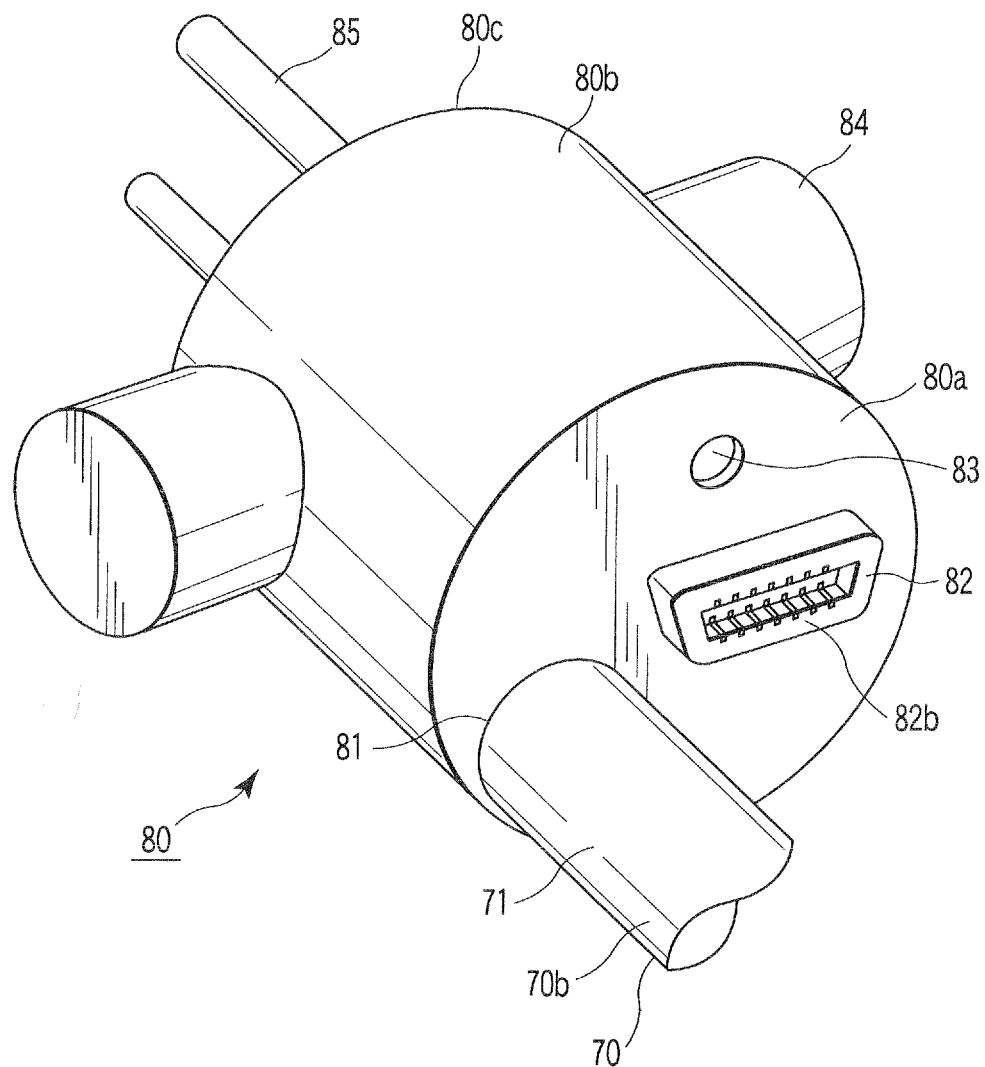
FIG. 3 is a perspective view of a connection unit.

An universal cord distal end portion 70a (endoscope main body 20 side of the universal cord 70) of the universal cord 70 close to the endoscope main body 20 is connected to the main body operation unit 61. Namely, the universal cord 70 is connected to the main body operation unit 61 at the universal cord distal end portion 70a. Further, as shown in FIG. 3, the universal cord 70 has a universal cord connector 71 at a proximal end portion 70b close to the connection unit 80. The universal cord connector 71 is a part to connect the connection unit 80. In this embodiment, the universal cord connector 71 is arranged at the proximal end portion 70b, fixed to the connection unit 80, and combined with (connected to) the connection unit 80 as one body. Therefore, the universal cord 70 is connected to the connection unit 80 as one unit by the universal cord connector 71. The main body operation unit 61 is connected to the connection unit 80 as one unit through the universal cord 70.

Next, the connection unit 80 will be explained by referring to FIG. 1 and FIG. 3. In FIG. 3, a stopper 82a is omitted for simplifying the illustration.

As shown in FIG. 3, the connection unit 80 has, on its end face 80a, a fixing part 81 to fix the universal cord connector 71, a concave connector 82 that is a part to connect a convex connector 108 of the imaging unit 100 described later, and a main unit illumination connector 83 that is a part to connect an imaging illumination connector 106 of the imaging unit 100 described later.

The concave connector 82 is a part to fit with the convex connector 108. Namely, by fitting the concave connector 82 with the convex connector 108, the imaging unit 100 is connected to the connection unit 80. The concave connector 82 has a contact 82b for the convex connector 108. The contact 82b is an elastic part, and is a stopper for the convex connector 108.

Figure 8C:
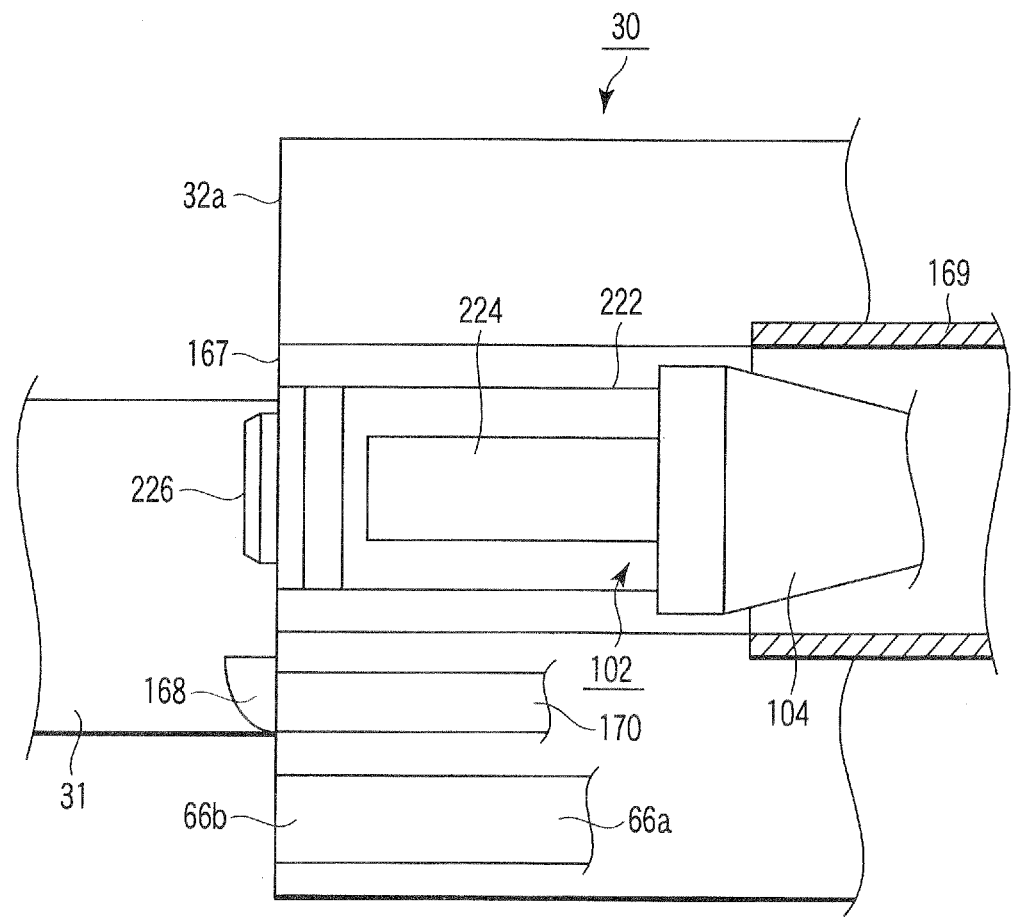
FIG. 8C is a schematic diagram showing an internal structure of a main body bending part.
Figure 8D:
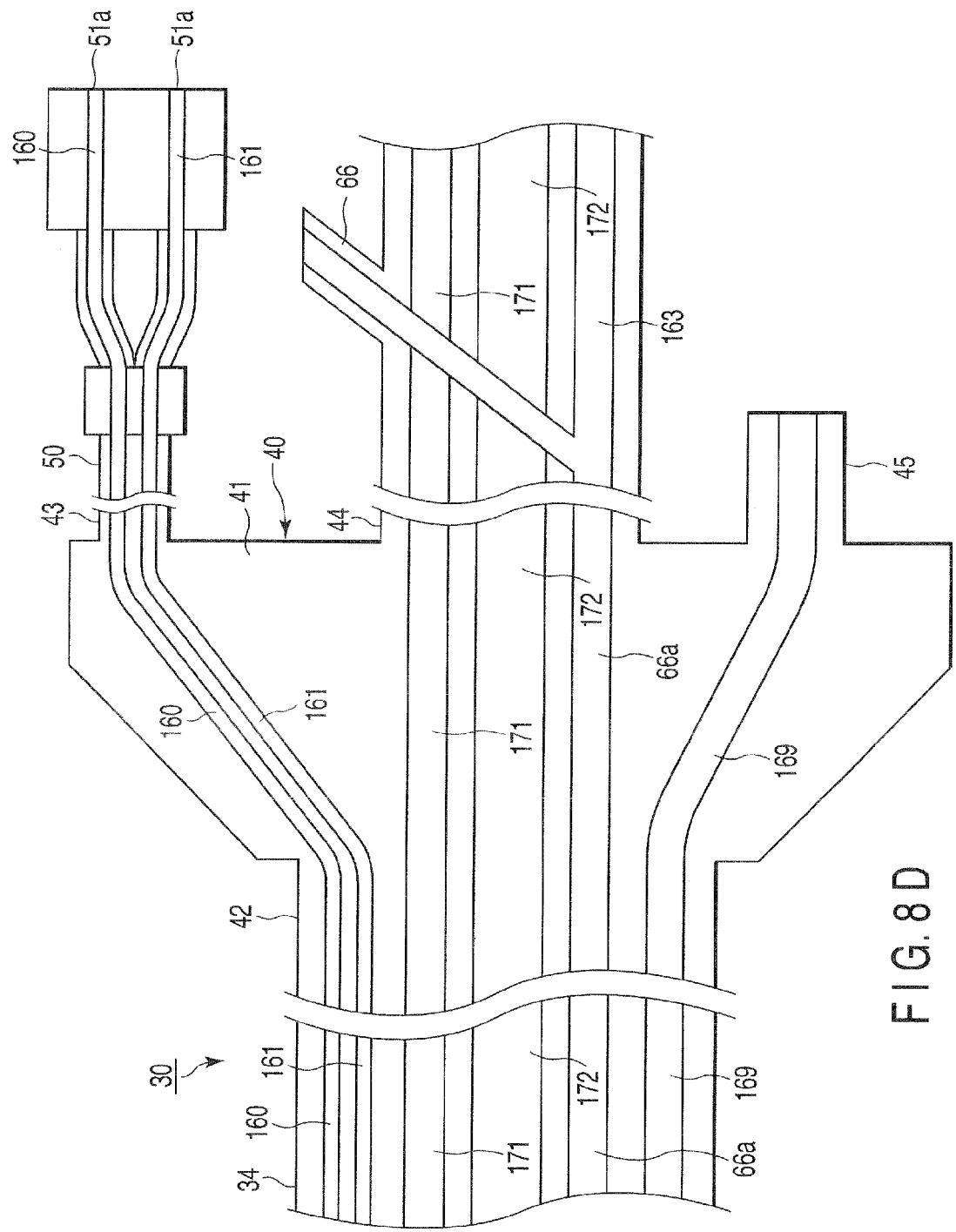
FIG. 8D is a schematic diagram showing an internal structure of an insertion part, a branch member, a first extension part, and a second extension part.
Figure 8E:
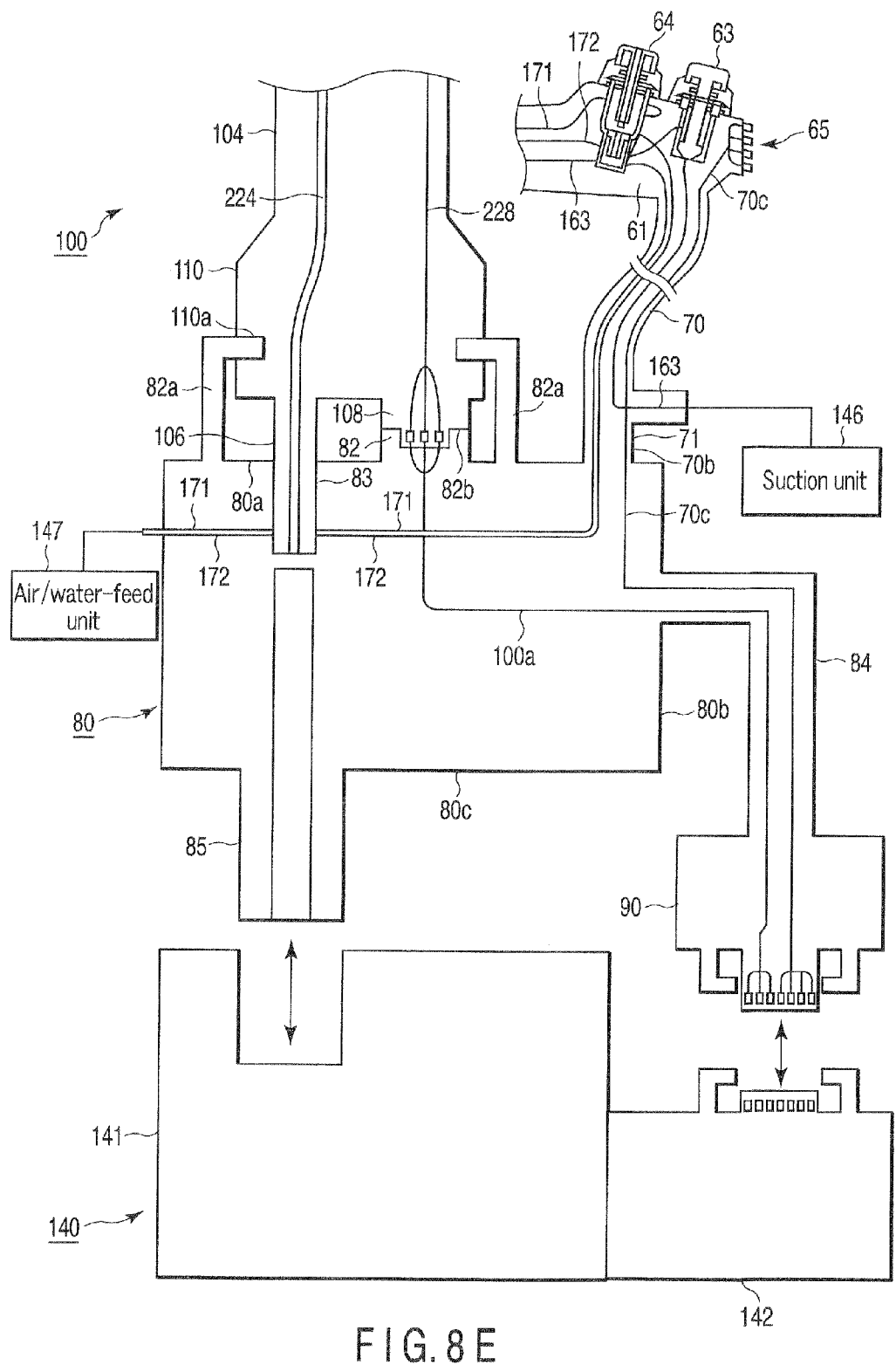
FIG. 8E is a schematic diagram showing a structure of connection between an endoscope and peripheral equipment, and an internal structure of a separate imaging connector, a main body operation unit, a universal cord, a connection unit, an imaging connector, and peripheral equipment.

The connection unit 80 has a stopper (a lock) 82a to prevent removal of the imaging unit 100 from the connection unit 80, when the concave connector 82 fits with the convex connector 108, as shown in FIG. 8E. The lock 82a is a claw, for example, and prevents removal by locking in a groove 110a in the separate imaging connector 110. The stopper 82a may be fixed with a screw. The stopper 82a may be provided in the concave connector 82 and convex connector 108.

The connector 80 has, on its side 80b, a lead-out part 84, which leads out electrical wiring 70c in the endoscope main body 20 including a signal conductor extended from the universal cord 70, and electrical wiring 100a in the imaging unit 100 including a signal conductor 228 extended from the imaging unit 100, to the imaging connector 90, as shown in FIG. 8E.

The connection unit 80 has, on the backside 80c, a peripheral equipment side connector 85, which is a part to make removable connection with a light source unit 141, an image display unit 143, and a control unit 144 in the peripheral equipment 140 to be described later. The backside 80c is positioned in the rear of the end face 80a.

As described above, the connection unit 80 connects the universal cord 70 through the fixing part 81 and universal cord connector 71, and connects the main body operation unit 61 through the universal cord 70. Namely, the connection unit 80 is provided in (connected as a part of) the endoscope main body 20 through the universal cord 70. The connection unit 80 connects the imaging unit 100 through the concave connector 82. The connection unit 80 has a peripheral equipment side connector 85, and connects the peripheral equipment 140 through the peripheral equipment side connector 85.

Next, the imaging unit 100 will be explained.

As shown in FIG. 1, the imaging unit 100 has an imaging module 102, a cable unit 104, a separate imaging connector 110, and a clamping member 114 functioning also as an adjustment unit.

The imaging module 102 and separate imaging connector 110 are connected through the cable unit 104. The imaging module 102 is provided at the distal end of the imaging unit 100. The separate imaging connector 110 is provided at the other end close to the connection unit 80 of the imaging unit 100, and is removably connected to the connection unit 80. The other end of the imaging unit 100 close to the connection unit 80 means a proximal end of the imaging unit 100.

A clamping member 114 is fit to the outside of the cable unit 104. The cable unit 104 and the imaging module 102 provided at the distal end of the imaging unit 100 (the clamping member 114) are inserted into the insertion part 30 from the third opening 45 through the branch member 40. At this time, the imaging module 102 is guided along a guide tube 169 explained later, and positioned at the distal end portion 32. The cable unit 104 arranged on the proximal end side of the imaging unit 100 (the clamping member 114) may be covered by an outer sheath.

Figure 4A:
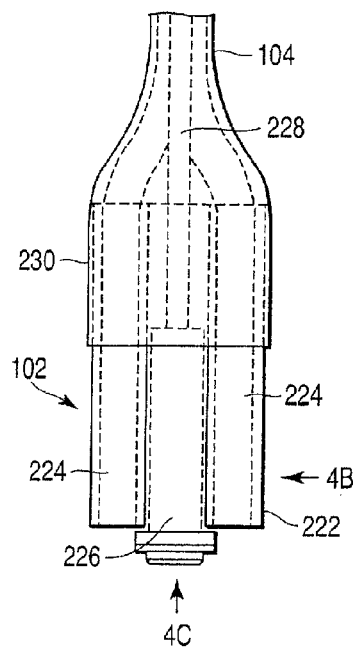
FIG. 4A is a top view of an imaging module.
Figure 4B:
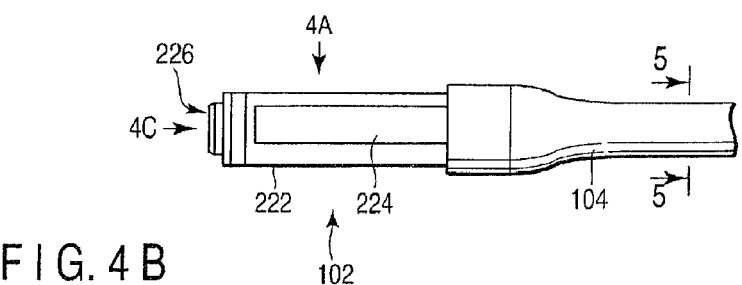
FIG. 4B is a side view of an imaging module.

As shown in FIGS. 4A and 4B, the imaging module 102 emits illumination light to a patient (a subject), and captures an observation image provided by the illumination light. The imaging module 102 is inserted into the insertion part 30, and is removably arranged in the rear of the distal end face 32a, as shown in FIG. 5C.

Figure 4C:
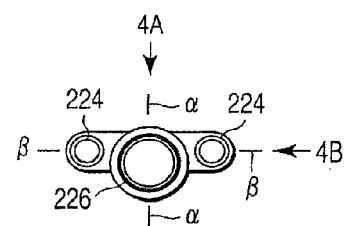
FIG. 4C is a front view of an imaging module.

The imaging module 102 has a casing 222 made of metallic material, for example. As shown in FIGS. 4A, 4B and 4C, the casing 222 contains a pair of light guide bundles (illumination optics) 224 for emitting illumination light, and an imaging unit 226 (including objective optics) for capturing an observation image. The imaging unit 226 is an objective lens, for example. The imaging unit 226 is arranged between the pair of light guide bundles 224.

The light guide bundle 224 is inserted into the cable unit 104, and arranged in the separate imaging connector 110. A proximal end portion of the light guide bundle 224 is connected to an imaging illumination connector 106 described later (refer to FIGS. 7 and 8E).

A proximal end portion of the imaging unit 226 provided in the casing 222 is connected to a signal conductor 228. The signal conductor 228 is inserted into the cable unit 104, and arranged in the separate imaging connector 110. A proximal end portion of the signal conductor 228 is connected to the convex connector 108 (refer to FIGS. 7 and 8E).

The casing 222 is formed symmetrical with respect to the line α-α in FIG. 4C, but asymmetrical with respect to the line β-β. Namely, the casing 222 has a direction. In this case, the center axis of the imaging unit 226 is arranged on the line α-α in FIG. 4C, and the center of the light guide bundle 224 exists at the position separated the equal distance from the center axis of the imaging lens 226. Thus, the casing 222 is formed symmetrical with respect to the line α-α in FIG. 4C. In contrast, the center axis of the light guide bundle 224 is arranged on the line β-β, and the center axis of the imaging unit 226 is displaced from the line β-β. Namely, the imaging module 102 has a part that is formed asymmetrical with respect to the axes on the plane orthogonal to the longitudinal direction of the imaging unit 100 (the longitudinal direction of the cable unit 104) (the line β-β in this embodiment). Thus, the casing 222 is formed asymmetrical with respect to the line β-β in FIG. 4C.

As described above, the direction of the imaging module 102 is defined. Therefore, when the imaging unit 100 is inserted into the insertion part 30, the direction of the imaging module 102 to the third opening 45 is easily determined by the appearance of the imaging module 102, etc. The shape of the third opening 45 may be similar to the shape of the imaging module 102. Thereby, the direction of the imaging module 102 to the third opening 45 is determined by the shapes of the third opening 45 and imaging module 102.

Figure 5:
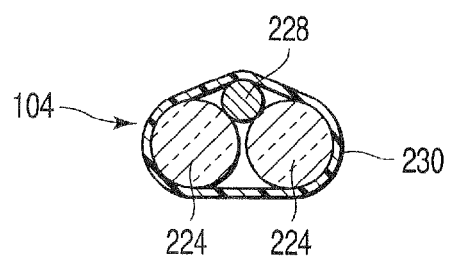
FIG. 5 is a transverse sectional view of a cable unit, taken along the line 5-5 in FIG. 4B.
Figure 6:
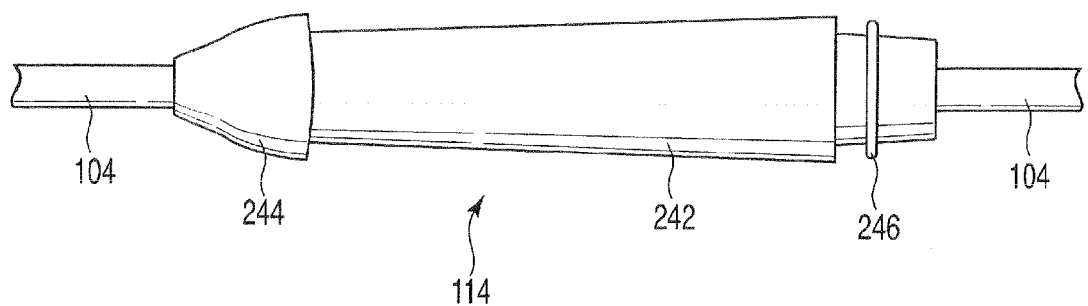
FIG. 6 is a view of a clamping member.

In this embodiment, the casing 222 is explained as symmetrical with respect to the line α-α described above, but it is also preferable that the casing 222 is asymmetrical with respect to the line β-β. As shown in FIG. 5, the cable unit 104 is formed like a cable, in which the pair of light guide bundles 224 and signal conductor 228 are inserted into a heat-shrinkable tube 230, for example. As shown in FIG. 1 and FIG. 6, the clamping member 114 is fit to the outside of the cable unit 104.

As shown in FIG. 6, the clamping member 114 has a cylindrical main body 242, and a heat-shrinkable tube 244, which is provided in the proximal end portion of the main body 242, combining the main body 242 and cable unit 104 as one unit. The main body 242 is made hard with resin material, rubber material or elastomer. A distal end of the main body 242 is formed like a pipe with a small diameter so as to be fit in the third opening 45. The distal end of the main body 242 has, on its outer periphery, a flange 246 to removably fit to the third opening 45. At this time, the imaging module 102 is being connected to the distal end portion 32.

The position of the flange 246 is adjusted at the third opening 45, whereby the position of the imaging unit 226 at the distal end portion 32 is adjusted in the longitudinal direction of the insertion part 30. Namely, the flange 246 is a part, which adjusts the position of the imaging unit 100 in the longitudinal direction of the insertion part 30, and adjusts the position of the imaging unit 226 in the longitudinal direction of the insertion part 30. In other words, the flange 246 adjusts the push-in depth of the imaging module 102 and cable unit 104.

As for the clamping member 114, instead of using the heat-shrinkable tube 244, or in addition to using the heat-shrinkable tube 244, a protective member such as a tube may be fit to the outer periphery of the cable unit 104, and the protective member may be secured to the inside surface of the main body 242 with an adhesive, for example. The clamping member 114 may be formed in a fixable shape by using a metallic member such as a screw and a spring.

Figure 7:
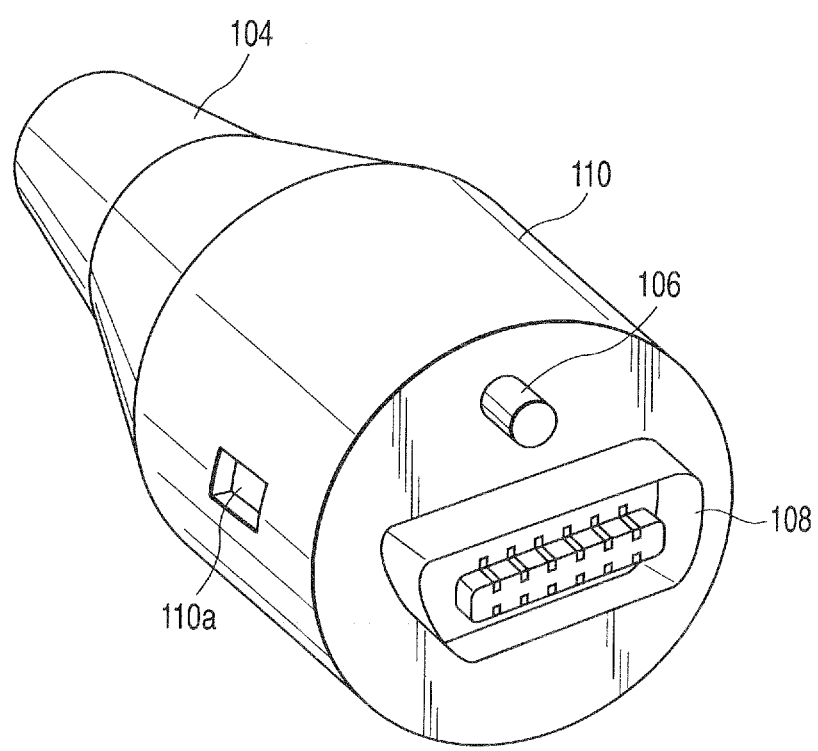
FIG. 7 is a perspective view of a separate imaging connector.

The separate imaging connector 110 is removably connected to the connection unit 80. As shown in FIG. 7, the separate imaging connector 110 has an imaging illumination connector 106, and a convex connector 108. The imaging illumination connector 106 and convex connector 108 are held as one piece in the separate imaging connector 110.

The imaging illumination connector 106 is connected to the proximal end portion of the light guide bundle 224 as described above (refer to FIG. 8E). When the separate imaging connector 110 is removably connected to the connection unit 80, the imaging illumination connector 106 is removably connected to the main unit illumination connector 83 (refer to FIG. 8E). When the imaging illumination connector 106 is connected to the main unit illumination connector 83, and the connection unit 80 is connected to the light source unit 141 in the peripheral equipment 140 through the peripheral equipment side connector 85, the light source unit 141 supplies illumination light to the light guide bundle 224. The illumination light is guided from the proximal end (the incident end) of the light guide bundle 224 to the distal end (the exit end). The illumination light is emitted from the distal end of the light guide bundle 224.

The convex connector 108 is connected to the signal conductor 228 as described above (refer to FIG. 8E), and connects the electrical wiring 100a to the connection unit 80. When the separate imaging connector 110 is removably connected to the connection unit 80, the convex connector 108 is removably fit in the concave connector 82 (refer to FIG. 8E). The convex connector 108 is a part to fit with the concave connector 82. Namely, by fitting the convex connector 108 in the concave connector 82, the imaging unit 100 is removabley connected to the connection unit 80.

As described above, the convex connector 108 is connected to the concave connector 82, and the imaging connector 90 connected to the connection unit 80 is connected to the image-processing unit 142 in the peripheral equipment 140. At this time, an observation image captured by the imaging unit 226 is displayed on a monitor 143a through the signal conductor 228, convex connector 108, concave connector 82, imaging connector 90, image-processing unit 142, and image display unit 143.

The separate imaging connector 110 has a groove 110a to catch the stopper 82a as shown in FIG. 7 and FIG. 8E.

Next, the peripheral equipment 140 will be explained.

As shown in FIG. 1, the peripheral equipment 140 has a light source unit 141 for generating illumination light for photographic shooting, an image-processing unit 142 for performing various image processing for an image captured by the imaging unit 100, an image display unit 143 having a monitor 143a, which is a display unit to display an image and image data (an image captured by the imaging unit 100, and processed by the image-processing unit 142), and states of the units and operations, a control unit 144 for controlling the whole endoscopic system 1, and performing arithmetic operations the whole endoscopic system 1, an input unit 145 having a keyboard, a suction unit 146, an air/water-feed unit 147 having an air/water-feed pump and a supply water tank.

Next, a brief explanation will be given of the internal structure of the endoscope 10, and the structure of connection between the endoscope 10 and peripheral equipment 140, with reference to FIGS. 8A to 8E.

As shown in FIG. 8A, exit ports 160a and 161a are provided on the distal end face 31a. Channel tubes 160 and 161 are arranged at the exit ports 160a and 161a. The channel tubes 160 and 161 are passed through the insertion part 30, branch member 40 and second extension part 50, and are extended to the channel opening 51a. A not-shown distal end treatment device is inserted into the channel opening 51a. The distal end treatment device inserted into the channel opening 51a is projected from the exit ports 160a and 161a through the channel tubes 160 and 161.

As shown in FIGS. 8B and 8C, a distal end opening 66b is provided on the distal end face 32a of the distal end portion 32. A channel tube 66a is arranged at the distal end opening 66b. The channel tube 66a is passed along the first extension part 60 through the main body bending part 33, flexible tube part 34 and branch member 40, and extended to the main body treatment device insertion part 66, as shown in FIGS. 8C and 8D. A not-shown main body treatment device is inserted into the main body treatment device insertion part 66. The main body treatment device inserted into the main body treatment device insertion part 66 is projected from the distal end opening 66b through the channel tube 66a. The distal end opening 66b functions also as a suction nozzle. The channel tube 66a is connected to a suction tube 163, which is a piping for suction, as shown in FIG. 8D. The suction tube 163 is inserted into the universal cord 70 through the main body operation unit 61, and is connected to the connection unit 80, as shown in FIG. 5E.

As shown in FIGS. 8B and 8C, the distal end face 32a is provided with a pair of illumination windows 166, an opening 167 in which the imaging unit 226 is provided, and an air/water-feed nozzle 168.

As shown in FIG. 8C, a guide tube 169 is fixed to the proximal end side of the opening 167. The distal end of the guide tube 169 is connected to the distal end portion 32. Or, the distal end of the guide tube 169 is set free in proximity to the distal end portion 32. The proximal end of the guide tube 169 is inserted into the main body bending part 33 and flexible tube part 34 as shown in FIG. 8D, and is connected to the branch member 40. The guide tube 169 guides the imaging module 102 and cable unit 104 inserted into the third opening 45, to the distal end portion 32.

As shown in FIG. 8C, an air/water-feed tube (an air/water-feed piping) 170 is fixed to the proximal end side of the air/water-feed nozzle 168. Further, in FIG. 8D, the proximal end of the air/water-feed tube 170 is branched to an air-feed tube 171 as an air-feed piping, and a water-feed tube 172 as a water-feed piping. As shown in FIG. 8D and FIG. 8E, the air-feed tube 171 and water-feed tube 172 are inserted into the universal cord 70 through the main body bending part 33, flexible tube part 34, branch member 40, first extension part 60, and main body operation unit 61. Further, the air-feed tube 171 and water-feed tube 172 are connected to the connection unit 80. As described above, the suction tube 163, air-feed tube 171 and water-feed tube 172 are inserted into the universal cord 70 and endoscope main body 20, and are connected to the connection unit 80. Namely, the suction tube 163, air-feed tube 171 and water-feed tube 172 are passed through (inserted) the endoscope main body 20.

As described above, the connection unit 80 is connected to the peripheral equipment 140 through the peripheral equipment side connector 85. Thereby, the connection unit 80 functions as a piping connector, which connects the suction tube 163, air-feed tube 171 and water-feed tube 172 inserted into the universal cord 70, to the peripheral equipment 140. Specifically, when the connection unit 80 connects the light source unit 141, image display unit 143 and control unit 144 in the peripheral equipment 140, the air-feed tube 171 and water-feed tube 172 are connected to the air/water-feed unit 147, and the suction tube 163 is connected to the suction unit 146.

The suction button 63, air/water-feed button and various buttons 65 are connected to the electrical wiring 70c in the endoscope main body 20 including respective signal conductors. The electrical wiring 70c is inserted into the universal cord 70, and is connected to the imaging connector 90 through the connection unit 80. The electrical wiring 100a in the imaging unit 100 including the signal conductor 228 extended from the imaging unit 100 is also connected to the imaging connector 90 through the connection unit 80. When the imaging connector 90 is connected to the image-processing unit 142 in the peripheral equipment 140, the electrical wirings 70c and 100a are connected to the image-processing unit 142. Namely, the imaging connector 90 is a wiring connector, which is branched from the connection unit 80, and connects the electrical wirings 400a in the imaging unit 100 and the electrical wirings 70c, to the image-processing unit 142 in the peripheral equipment 140.

Next, a method of operating this embodiment will be explained.

When the endoscope 10 is used, the imaging module 102 and cable unit 104 are inserted into the third opening 45, guided to the distal end portion 32 along the guide tube 169, and set in the distal end portion 32.

When the imaging module 102 is set in the distal end portion 32, the flange 246 is fit to the third opening 45. Thus, the imaging unit 100 is positioned with respect to the endoscope main body 20.

The separate imaging connector 110 is connected to the connection unit 80. Thereby, the imaging illumination connector 106 is connected to the main unit illumination connector 83, and the convex connector 108 is fit with the concave connector 82.

At this time, the stopper 82a locks in the groove 110a. This prevents removal of the imaging unit 100 from the connection unit 80.

Thereby, the endoscope 10 is formed. When the endoscope 10 is connected to the peripheral equipment 140, the connection unit 80 is connected to the peripheral equipment 140 which contains the light source unit 141, image display unit 143 and control unit 144 through the peripheral equipment side connector 85, and the imaging connector 90 is also connected to the peripheral equipment 140 which contains the image-processing unit 142.

The insertion part 30 is inserted into an abdominal cavity in this state. When the distal end operation unit 51 is operated, the distal end bending part 31 is operated and bent. When the main body operation unit 61 is operated, the main body bending part 33 is operated and bent. The distal end treatment device is inserted into the channel tubes 160 and 161 through the channel opening 51a, aid is projected from the exit ports 160a and 161a. A not-shown main body treatment device is inserted into the channel tube 66a through the main body treatment insertion part 66, and is projected from the distal end opening 66b. Thereby, the treatment device can treat an affected part in the abdominal cavity. The air/water-feed unit 147 ejects air and liquid from the air/water nozzle 168 through the air-feed tube 171 or water-feed tube 172, for cleaning the observation window of the imaging unit 226. The air and liquid are sucked from the distal end opening 66b by the suction unit 146 through the channel tube 66a and suction tube 163.

After the treatment is finished, the insertion part 30 is removed from the abdominal cavity, the flange 246 is detached from the third opening 45, and the imaging unit 100 is removed from the insertion part 30. The connection unit 80 and imaging connector 90 are disconnected from the peripheral equipment 140. The separate imaging connector 110 is disconnected from the connection unit 80. The endoscope main body 20 is disposed, or reused after cleaning and disinfections. The imaging unit 100 is reused after cleaning and disinfections.

As described above, in this embodiment, as the connection unit 80 is connected to the peripheral equipment 140 after connecting the separate imaging connector 110 and the connection unit 80, it is unnecessary to directly connect the imaging unit 100 to the peripheral equipment 140. Namely, in this embodiment, it is unnecessary to provide a connection unit for connecting the imaging unit 100 to the peripheral equipment 140.

Therefore, in this embodiment, as the endoscope 10 is connected to the peripheral equipment 140 only through the connection unit 80, the endoscope 10 can easily be connected to the peripheral equipment 140.

Further, in this embodiment, by connecting the connection unit 80, which is already connected to the separate imaging connector 110, to the peripheral equipment 140, the endoscope main body 20 and imaging unit 100 can be connected to the peripheral equipment 140. Thereby, in this embodiment, the endoscope 10 and imaging unit 100 can be connected to the peripheral equipment 140 in one operation.

Further, in this embodiment, as the endoscope main body 20 and imaging unit 100 are connected to the peripheral equipment 140 at one point through the connection unit 80, not separately connected, and the connection can be speedy made free from misconnection.

The imaging unit 100 can easily be separated from the endoscope main body 20 by disconnecting the separate imaging connector 110 from the connection unit 80, and the imaging unit 100 can be easily replaced.

Besides, the branch member 40 is provided, and the third opening 45 is provided for inserting/removing the imaging module 102 into/from the branch member 40. Therefore, in this embodiment, when the imaging unit 100 is connected to the endoscope main body 20, the imaging module 102 can easily be inserted into the insertion part 30 simply by inserting the imaging module 102 into the third opening 45.

When the imaging unit 100 is removed from the endoscope main body 20, the imaging module 102 can easily be removed through the third opening 45.

Therefore, in this embodiment, the endoscope main body 20 and imaging unit 100 can be separately cleaned and disinfected. Or, the endoscope 20 can be disposed, and only the imaging unit 100 can be cleaned and disinfected. Therefore, it is possible to use the imaging unit 100 more efficiently by connecting the imaging unit 100 to another endoscope body 20 while one endoscope main body 20 is being cleaned and disinfected.

Besides, in this embodiment, by reducing the length of the imaging unit 100, a noise can be prevented in the imaging unit 100, and a clear image can be displayed on the monitor 143a. Further, by reducing the length of the imaging unit 100, decrease in brightness of the illumination light supplied from the light source unit 141 to the light guide bundle 224 can be prevented.

In this embodiment, the imaging unit 100 has a light guide bundle 224 and imaging unit 226, but only the imaging unit 226 may be provided. In this case, the light guide bundle 224 that is illumination optics may be connectable to and separable from the endoscope main body 20, like the imaging unit 100.

Next, a second embodiment of the invention will be explained with reference to FIG. 9 to FIG. 12. The same components as those of the first embodiment are denoted by the same reference numbers, and a description thereof is omitted.

Figure 9:
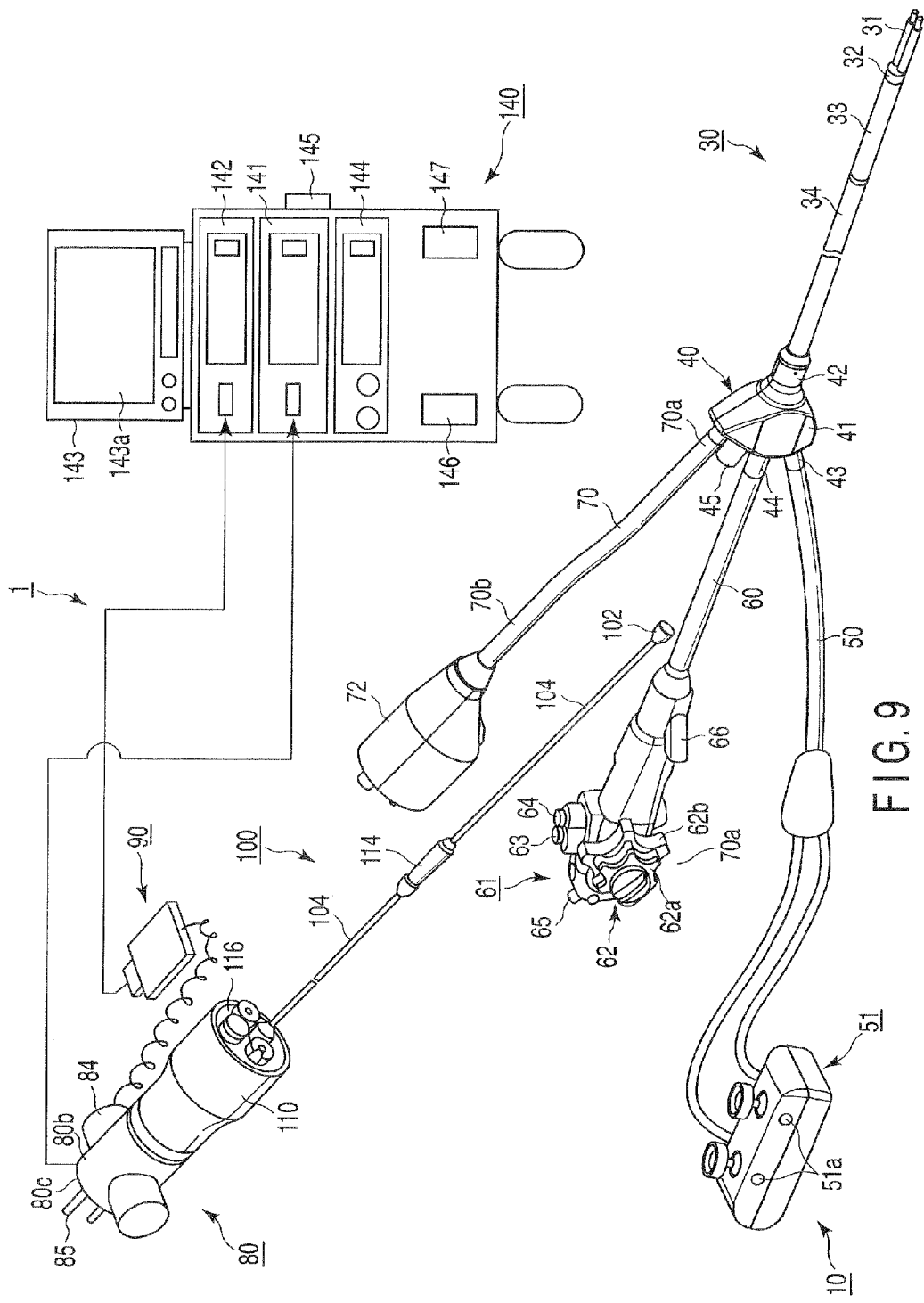
FIG. 9 is a diagram showing a configuration of an endoscopic system according to a second embodiment of the invention.

In the second embodiment, as shown in FIG. 9, the imaging unit 100 is previously fixed to the connection unit 80 through the separate imaging connector 110. The universal cord distal end portion 70a close to the endoscope main body 20 is not connected to the main body operation unit 61, and connected to the branch member 40. The proximal end portion 70b of the universal cord 70 (a universal cord connector 72 in this embodiment) is removably connected to the separate imaging connector 110. The separate imaging connector 110 in this embodiment has a separate universal cord connector 116, which is a part to connect the proximal end portion 70b of the universal cord 70.

Figure 10:
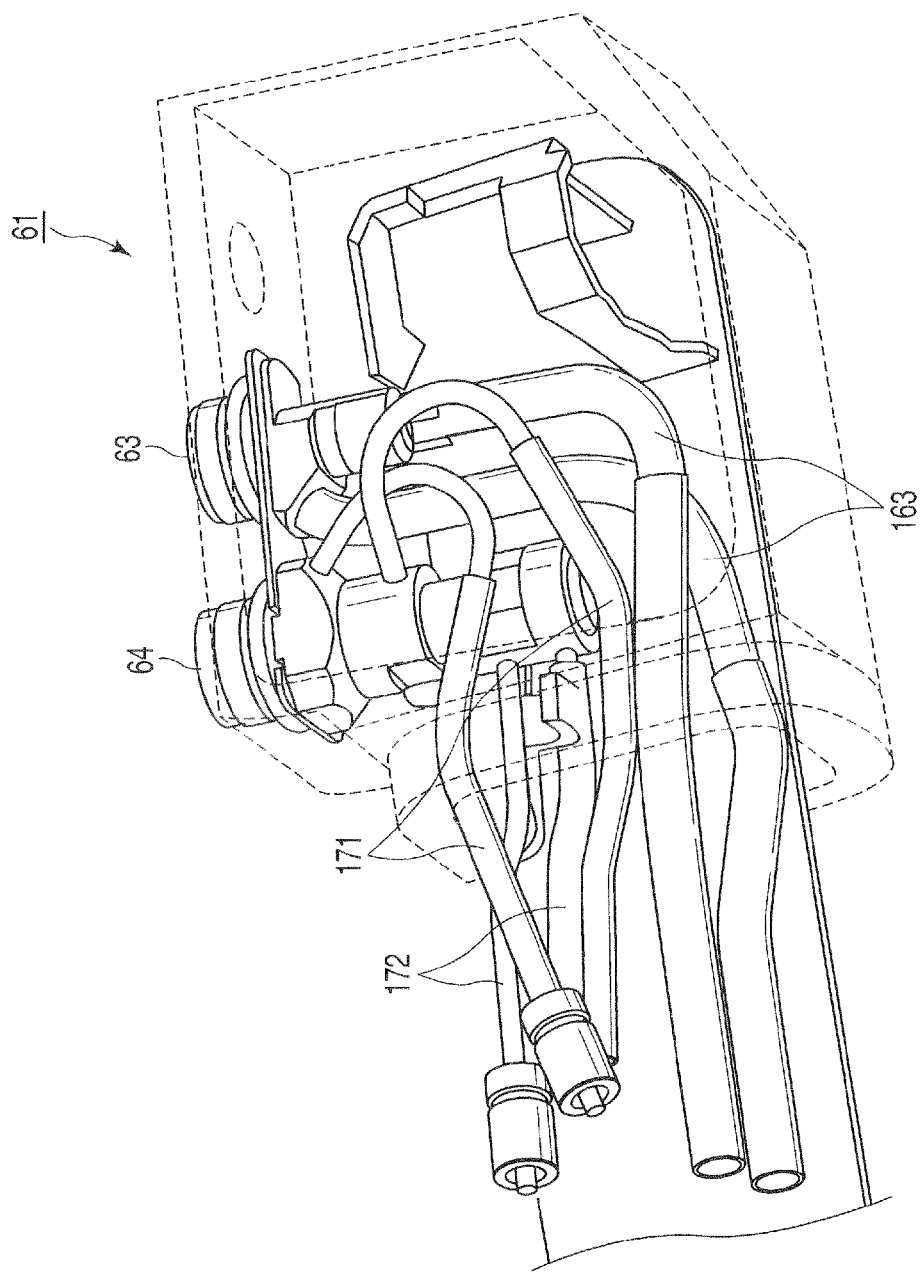
FIG. 10 is a diagram showing a folded state of an air-feed tube, a water-feed tube, and a suction tube in a main body operation unit.
Figure 11:
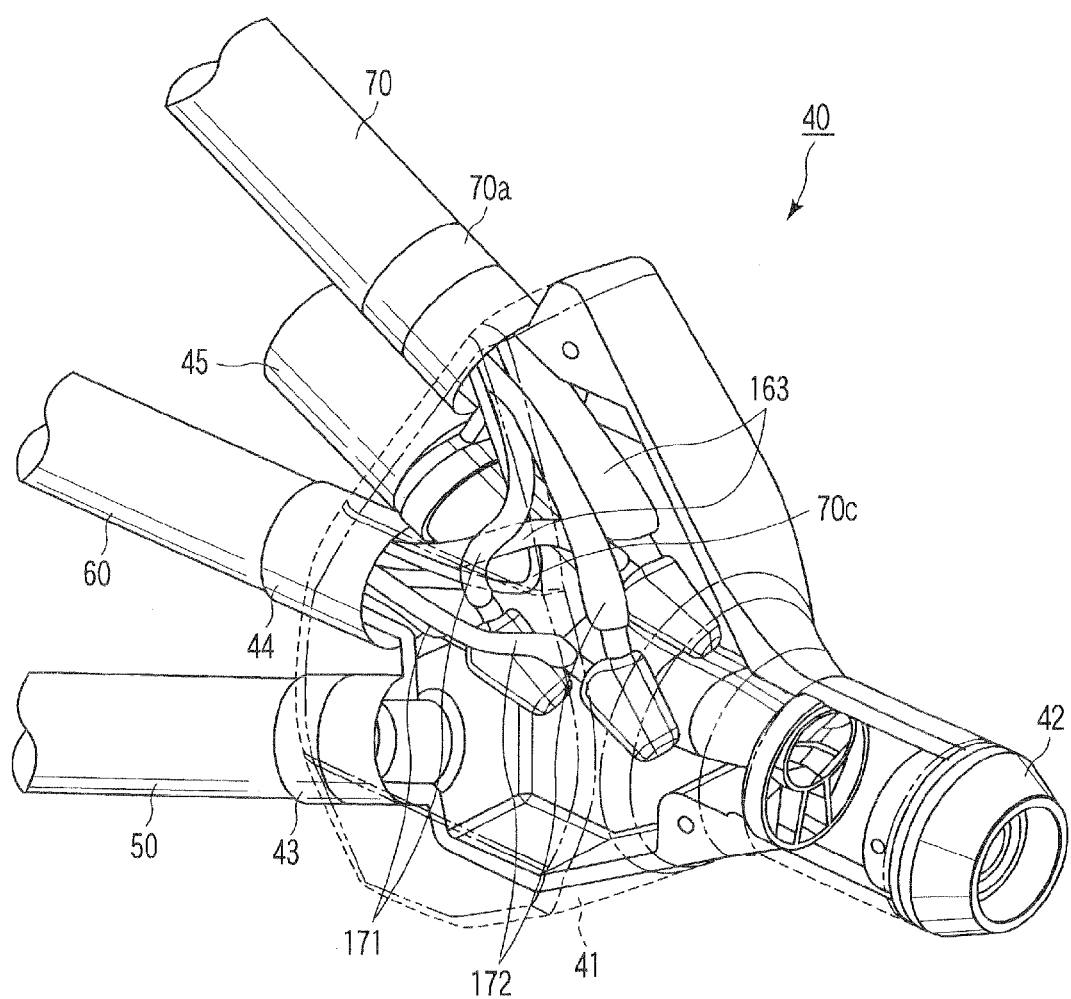
FIG. 11 is a diagram showing a folded state of an air-feed tube, a water-feed tube, a suction tube, and a signal conductor in a branch member.

The universal cord distal end portion 70a is connected to the branch member 40. Thus, the air-feed tube 171, water-feed tube 172 and suction tube 163 are passed through the distal end portion 32, main body bending part 33, flexible tube part 34, branch member 40 and first extension part 60, to the main body operation unit 61, as in the first embodiment. In the second embodiment, the air-feed tube 171, water-feed tube 172 and suction tube 163 are folded in the main body operation unit 61, as shown in FIG. 10, and are passed from the main body operation unit 61 to the branch member 40 through the first extension part 60. Further, the air-feed tube 171, water-feed tube 172 and suction tube 163 are folded in the branch member 40, and are inserted into the universal cord 70 as shown in FIG. 11.

Further, the electrical wiring 70c including signal conductors connected to the suction button 63, air/water-feed button 64 and various buttons 65 is passed from the main body operation unit 61 to the branch member 40 through the extension part 60, folded in the branch member 40, and inserted into the universal cord 70.

The universal cord 70 has, at the proximal end portion 70b, a universal cord separation connector 72, which is a part to removably connect the separate imaging connector 110 (the separate universal cord connector 116). The universal cord separation connector 72 holds the air-feed tube 171, water-feed tube 172 and suction tube 163, which are passed through the universal cord 70.

Figure 12:
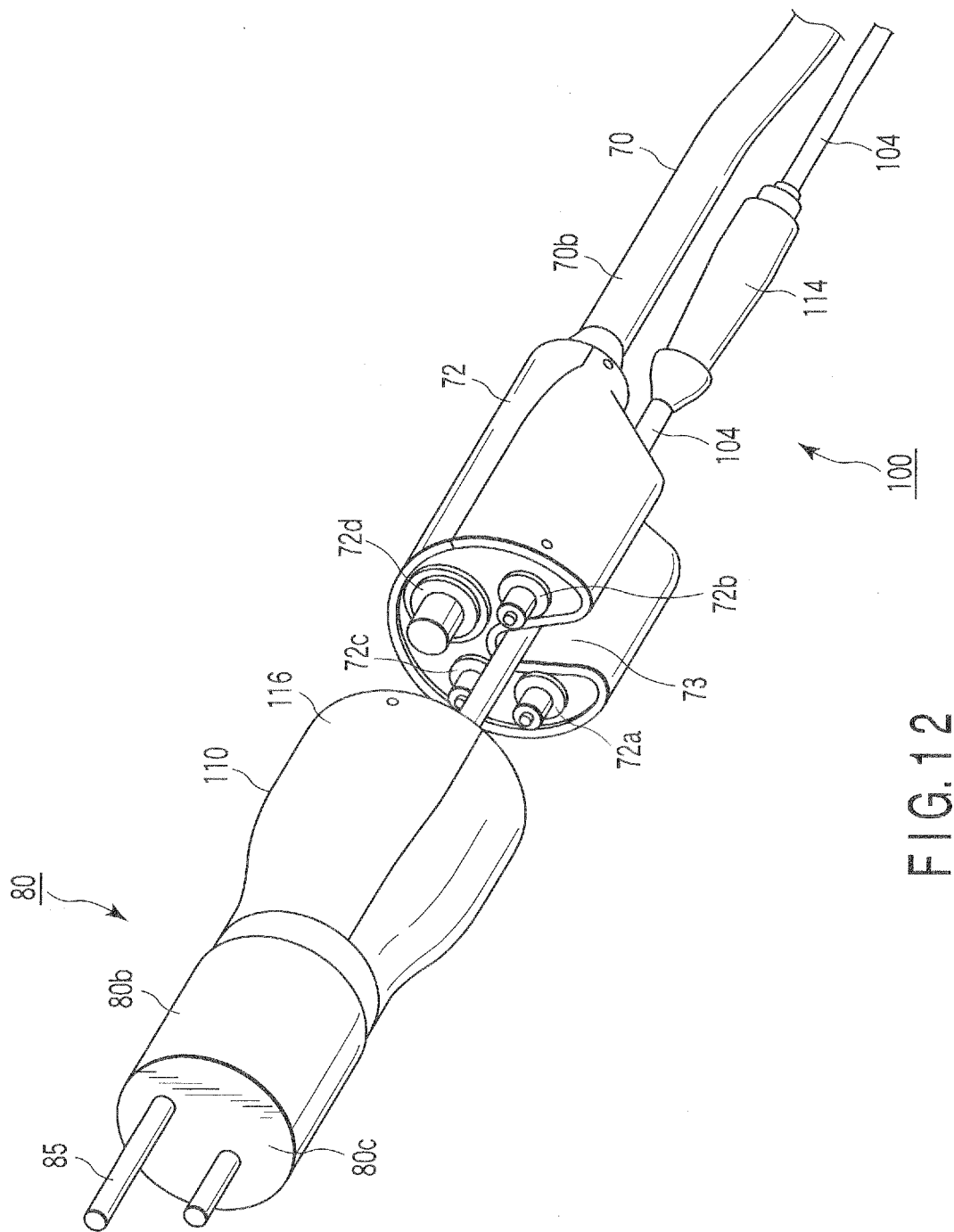
FIG. 12 is a perspective view of a universal cord separation connector.

Further, as shown in FIG. 12, the universal cord separation connector 72 has an air-feed connector 72a, which connects the air-feed tube 171 to the separate imaging connector 110, and connects the air-feed tube 171 to the peripheral equipment 140 through the connection unit 80; a water-feed connector 72b, which connects the water-feed tube 172 to the separate imaging connector 110, and connects the water-feed tube 172 to the peripheral equipment 140 through the connection unit 80; a suction connector 72c, which connects the suction tube 163 to the separate imaging connector 110, and connects the suction tube 163 to the peripheral equipment 140 through the connection unit 80; and electrical wiring connector 72d, which connects the electrical wiring 70c to the peripheral equipment 140 through the imaging connector 90. As shown in FIG. 12, the universal cord separation connector 72 has a recess 73, which catches the cable unit 104, slides the cable unit 104 to the separate imaging connector 110, and guides the imaging unit 100, when making connection with the separate imaging connector 110.

Next, a method of operating this embodiment will be explained.

When the endoscope 10 is used, the imaging module 102 and cable unit 104 are inserted into the third opening 45, guided to the distal end portion 32 by the guide tube 169, and set in the distal end portion 32, as in the first embodiment.

When the imaging module 102 is set in the distal end portion 32, the flange 246 is fit to the third opening 45. Thus, the imaging unit 100 is positioned with respect to the endoscope main body 20.

Next, the universal cord separation connector 72 slides the cable unit 104 to the separate imaging connector 110 in the recess 73, and connects the separate imaging connector 110 through the separate universal cord connector 116.

Connection of the connection unit 80 to the peripheral equipment 140 is substantially the same as in the first embodiment, and a detailed explanation thereof is omitted.

As described above, in this embodiment, as the universal cord distal end portion 70a is connected to the branch member 40, and the universal cord 70 is not connected to the main body operation unit 61, the main body operation unit 61 can be made light in weight. Thus, in this embodiment, an operator's fatigue in operating the main body operation unit 61 can be reduced, and operability of the endoscope 10 in making treatment can be kept high.

Further, in this embodiment, by extending the universal cord 70 to a desired length, the peripheral equipment 140 can be set apart from an operator and patient. The universal cord 70 cannot be infinitely extended, because a transmission cable (e.g. the signal conductor 228 and electrical wiring 70c, 100a) in the imaging unit 226 is affected by a noise. However, in the configuration of this embodiment, the universal cord 70 can be routed with a high degree of flexibility, and the peripheral equipment 140 can be set apart from an operator and patient by a desired distance. In this embodiment, an operator and patient are prevented from contacting the main body operation unit 61 and peripheral equipment 140, and are prevented from contamination by contacting the peripheral equipment 140, ensuring cleanliness of an operator and patient.

In this embodiment, suction and air/water-feed may be controlled by opening and closing a not-shown cylinder by turning on and off the suction button 63 and air/water-feed button 64. Suction and air/water-feed may also be controlled by opening and closing a not-shown control valve provided in the suction tube 163, air-feed tube 171, water-feed tube 172, air/water-feed unit 147 and the suction unit 146, by the ON/OFF signals of the suction button 63 and air/water-feed button 64.

Figure 13:
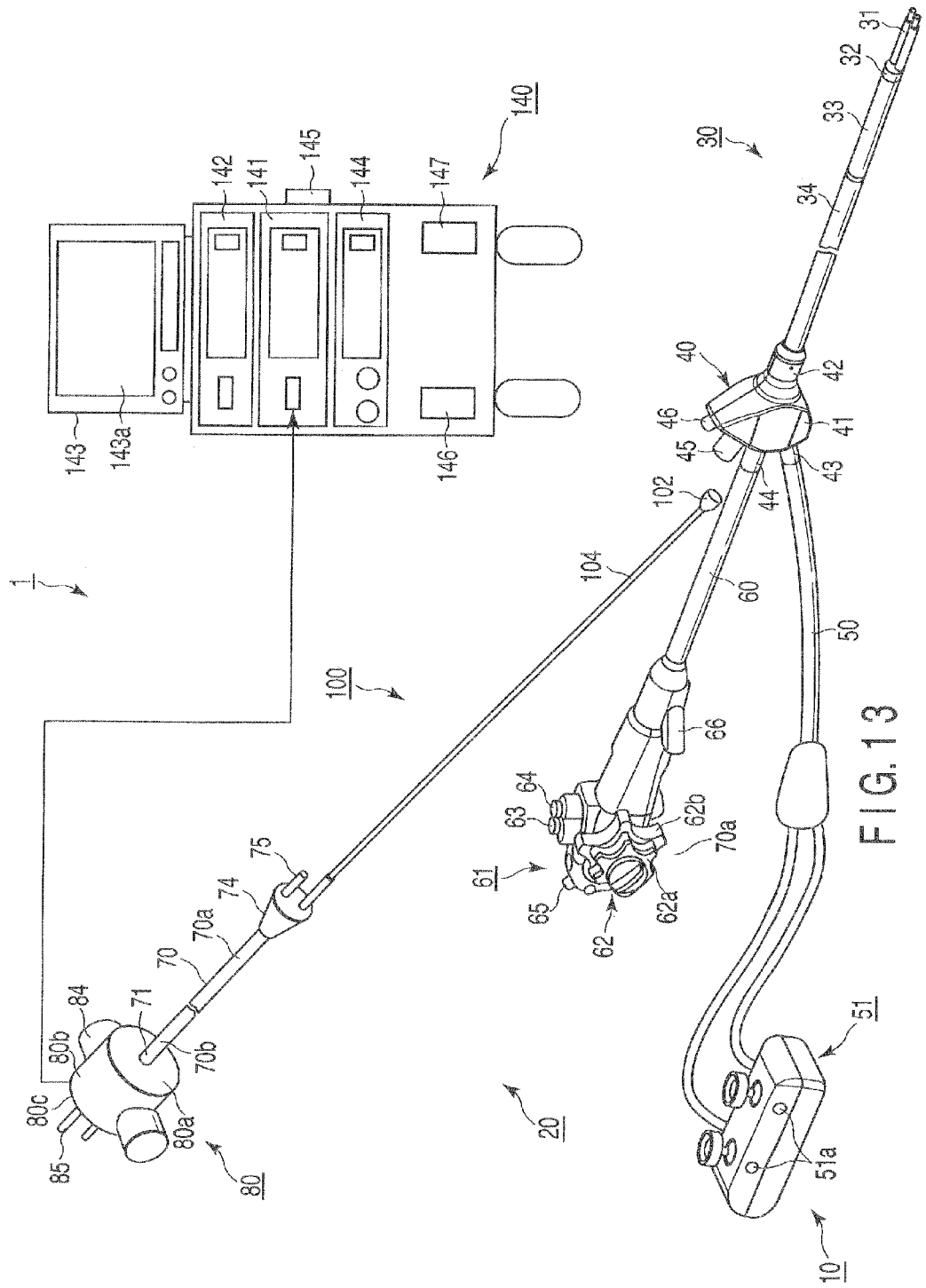
FIG. 13 is a diagram showing a configuration of an endoscope according to a third embodiment.

Next, a third embodiment of the invention will be explained with reference to FIG. 13. The same components as those of the first embodiment are denoted by the same reference numbers as in the first and second embodiments, and a description thereof is omitted.

In the third embodiment, the connection unit 80 is combined with or incorporated in the imaging connector 90, for example. Namely, the connection unit 80 and imaging connector 90 are made as one unit.

The air-feed tube 171, water-feed tube 172 and electrical wiring 70c are folded in the main body operation unit 61 and branch member 40, as in the second embodiment.

The universal cord 70 in this embodiment is connected to the connection unit 80 in the proximal end portion 70b by the universal cord connector 71, but is not connected to the main body operation unit 61 in the universal cord distal end portion 70a, as in the second embodiment.

The universal cord distal end portion 70a close to the endoscope main body 20 in this embodiment is provided with a single-body connector 74, which is removably connected to the branch member 40.

The single-body connector 74 is connected to the imaging unit 100 as one unit. Namely, the single-body connector 74 is a part to connect the universal cord 70 and imaging unit 100 as one unit. Namely, the connection unit 80, universal cord 70, imaging unit 100 and imaging connector 90 are constructed as one unit.

The single-body connector 74 is provided with a universal cord side channel connector 75 for connecting the air-teed tube 171, water-feed tube 172 and electrical wiring 70c on the universal cord 70 side, to the air-feed tube 171, water-feed tube 172 and electrical wiring 70c on the branch member 40 side, respectively. Namely, the universal cord side channel connector 75 connects air-feed tube 171, water-feed tube 172 and electrical wiring 70c on the branch member 40 side, to the peripheral equipment 140 through the universal cord 70 and connection unit 80. The branch member 40 is provided with a branch side channel connector 46 for connecting the universal cord side channel connector 75.

The single-body connector 74 functions also as a flange 246. By adjusting the position of the single-body connector 74 in the universal cord side channel connector 75, the position of the imaging unit 226 in the distal end portion 32 is adjusted in the longitudinal direction of the insertion part 30. The single-body connector 74 is a part, which adjusts the position of the imaging unit 100 in the longitudinal direction of the insertion part 30, and adjusts the position of the imaging unit 226 in the longitudinal direction of the insertion part 30. In other words, the push-in depth of the imaging module 102 and cable unit 104 is adjusted depending on the position of the single-body connector 74.

Therefore, the imaging unit 100 has only the imaging module 102 and cable unit 104.

Next, a method of operating this embodiment will be explained.

When the endoscope 10 is used, the imaging module 102 and cable unit 104 are inserted into the third opening 45, guided to the distal end portion 32 by the guide tube 169, and set in the distal end portion 32, as in the first embodiment.

At this time, the universal cord side channel connector 75 is connected to the branch side channel connector 46.

Thereby, the air-feed tube 171, water-feed tube 172 and electrical wiring 70c on the universal code 70 side are connected to the air-feed tube 171, water-feed tube 172 and electrical wiring 70c, respectively on the endoscope main body 20 side.

Connection of the connection unit 80 to the peripheral equipment 140 is substantially the same as in the first embodiment, and a detailed explanation thereof is omitted.

In this embodiment, the connection unit 80, universal cord 70 and imaging unit 100 are constructed as one unit. Therefore, it is unnecessary to connect the connection unit 80 to the imaging unit 100. Further, in this embodiment, the connection unit 80 and imaging connector 90 are constructed as one unit. Therefore, all the necessary operation is to connect the connection unit 80 to the peripheral equipment 140, and it is unnecessary to connect the imaging connector 90 to the peripheral equipment 140. As described above, in this embodiment, the endoscope 10 can easily be connected to the peripheral equipment 140, eliminating a connection operation, and the user's load can be reduced.

Further, in this embodiment, the universal code 70 is not connected to the main body operation unit 61 as in the second embodiment, and the operation unit can be made light in weight. Therefore, the operator's left-arm's fatigue can be reduced, and operability of the endoscope 10 in making treatment can be kept high.

Further, in this embodiment, the peripheral equipment 140 can be set apart from an operator and patient by a desired distance as in the second embodiment, and an operator and patient are prevented from contacting the main body operation unit 61 and peripheral equipment 140, and are prevented from contamination by contacting the peripheral equipment 140, ensuring cleanliness of an operator and patient.

In this embodiment, a so-called flexible endoscope with a bendable insertion part is described, but a similar embodiment can be applied to a so-called hard endoscope.

As described herein, the invention is not limited to the described embodiments. The invention may be embodied by modifying the constituent elements when practiced without departing from its spirit and essential characteristics. The invention may be embodied in other specific forms by appropriately combining the constituent elements disclosed in the embodiments described herein.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic system comprising:
an endoscope main body in which an air-feed piping, a liquid-feed piping and a suction piping are inserted, said endoscope main body having an insertion part that is insertable into an abdominal cavity;
an imaging unit which is connectable to and separable from the endoscope main body;
a branch member which is provided in a proximal end portion of the insertion part of the endoscope main body, said branch member having an opening for freely inserting and removing the imaging unit into and from the insertion part of the endoscope main body, when the imaging unit is connected to or separated from the endoscope main body;
a peripheral equipment which has a light source unit for generating illumination light for photographic shooting, and an image display unit for displaying an image captured by the imaging unit;
a piping connector which is provided in the endoscope main body through a universal cord in which the air-feed piping, the liquid-feed piping and the suction piping are inserted, wherein said piping connector is connectable to the imaging unit, has a peripheral equipment side connector to connect to the peripheral equipment, and is adapted to connect the air-feed piping, liquid-feed piping and suction piping inserted into the universal cord, to the peripheral equipment, by connecting to the peripheral equipment through the peripheral equipment side connector;
a universal cord connector which is provided on a piping connector side of the universal cord, and which is adapted to connect to the piping connector;
a separate imaging connector which is provided on a piping connector side of the imaging unit, and which is adapted to connect to the piping connector;
a wiring connector which is branched from the piping connector, and which is adapted to connect electrical wiring in the imaging unit and electrical wiring in the endoscope main body, to the peripheral equipment; and
a guide tube which is disposed inside the insertion part, the guide tube having a distal end portion fixed to a distal end portion of the insertion part and a proximal portion disposed in the insertion part to connect to the opening of the branch member;
wherein, when the imaging unit is connected to the endoscope main body, the imaging unit is inserted into the insertion part from the opening of the branch member and guided by the guide tube to the distal end portion of the insertion part from the opening of the branch member; and
wherein, when the imaging unit is separated from the endoscopic main body, the imaging unit is guided by the guide tube to the opening from the distal end portion of the insertion part and removed from the insertion part.

2. The endoscopic system according to claim 1, wherein the piping connector has a lead-out part which is adapted to lead out the electrical wiring in the imaging unit and the electrical wiring in the endoscope main body, to the wiring connector.

3. The endoscopic system according to claim 2, wherein the separate imaging connector has a convex connector to connect the electrical wiring in the imaging unit to the piping connector, the piping connector has a concave connector to connect to the convex connector, and the concave connector has a fitting part to fit with the convex connector.

4. The endoscopic system according to claim 3, wherein the piping connector has a stopper to prevent removal of the imaging unit from the piping connector, when the concave connector is fitted with the convex connector.

5. The endoscopic system according to claim 4, wherein the universal cord connector is connected to the piping connector as one body, and the piping connector is connected to the universal cord as one body through the universal cord connector.

6. The endoscopic system according to claim 5,
wherein the endoscope main body has a bending part;
wherein the endoscopic system further comprises an operation unit which is operable to operate the bending part of the endoscope main body; and wherein the operation unit is fixed to a proximal end of the endoscope main body, and an endoscope main body side of the universal cord is adapted to be connected to the operation unit.

7. The endoscopic system according to claim 1, wherein the universal cord connector is removable from the separate imaging connector, and an endoscope main body side of the universal cord is connected to the branch member.

8. The endoscopic system according to claim 7, wherein the universal cord connector has:
- an air-feed connection part which connects the air-feed piping to the peripheral equipment through the piping connector;
- a liquid-feed connection part which connects the liquid-feed piping to the peripheral equipment through the piping connector;
- a suction connection part which connects the suction piping to the peripheral equipment through the piping connector; and
- an electrical wiring connection part which connects the electrical wiring in the endoscope main body to the peripheral equipment through the wiring connector.

9. The endoscopic system according to claim 8, wherein the universal cord connector has a recess which catches the imaging unit, slides the imaging unit to the separate imaging connector, and guides the imaging unit, when making connection with the separate imaging connector.

10. The endoscopic system according to claim 8, wherein the air-feed piping, liquid-feed piping and suction piping are passed from a distal end to a proximal end of the endoscope main body, folded toward the branch member at the proximal end, folded toward the universal cord in the branch member, and inserted into the universal cord.

11. The endoscopic system according to claim 10, wherein the electric wiring, which is arranged on the proximal end side of the endoscope main body, and includes a signal conductor used for air/water feeding and suction, is passed from the proximal end to the branch member, folded toward the universal cord in the branch member, and inserted into the universal cord.

12. The endoscopic system according to claim 10, wherein the piping connector, universal cord, imaging unit and wiring connector are connected as one unit, and the endoscope main body side of the universal cord has a universal cord side channel connector, which connects the air-feed piping, liquid-feed piping and suction piping of the branch member, to the peripheral equipment through the universal cord and piping connector.

* * * * *